United States Patent [19]
Mordon et al.

[11] Patent Number: 6,086,580
[45] Date of Patent: Jul. 11, 2000

[54] LASER TREATMENT/ABLATION OF SKIN TISSUE

[75] Inventors: Serge Mordon, Villeneuve d'Ascq; Chryslain Sumian, Antibes; Karine Buffard, Mougins; Franck Pitre, Antibes; Martine Bouclier, Valbonne, all of France

[73] Assignee: Centre International de Recherches Dermatologiques, Valbourne, France

[21] Appl. No.: 08/986,145

[22] Filed: Dec. 5, 1997

[30] Foreign Application Priority Data

Dec. 5, 1996 [FR] France ................................. 96 14954

[51] Int. Cl.$^7$ .................................................... A61B 18/20
[52] U.S. Cl. ...................................... 606/9; 606/3
[58] Field of Search .............................................. 606/3, 9

[56] References Cited

U.S. PATENT DOCUMENTS

| | | | |
|---|---|---|---|
| 5,217,455 | 6/1993 | Tan .............................................. | 606/3 |
| 5,403,306 | 4/1995 | Edwards et al. ............................. | 606/3 |
| 5,423,803 | 6/1995 | Tankovich et al. . | |
| 5,425,728 | 6/1995 | Tankovich .................................... | 606/9 |
| 5,735,844 | 4/1998 | Anderson et al. ........................... | 606/9 |
| 5,766,214 | 6/1998 | Mehl, Sr. et al. ........................... | 606/9 |

FOREIGN PATENT DOCUMENTS

| | | |
|---|---|---|
| 0649667 | 4/1995 | European Pat. Off. . |
| 91/18646 | 12/1991 | WIPO . |
| 94/26184 | 11/1994 | WIPO . |
| 96/41657 | 12/1996 | WIPO . |

OTHER PUBLICATIONS

Selected Papers on Optical Fibers in Medicine, Spie Optical Engineering Press, Jan. 1, 1990, Bellingham, Washington; pp. 53–63, XP000467432, Parrish & Deustch, "Laser Photomedicine".

Selected Papers on Optical Fibers in Medicine, Spie Optical Engineering Press, Jan. 1, 1990, Bellingham, Washington; pp. 482–491,XP000467841, Brown, "Phototherpy of tumors".

*Primary Examiner*—John P. Leubecker
*Attorney, Agent, or Firm*—Burns, Doane, Swecker & Mathis, L.L.P.

[57] ABSTRACT

Mammalian skin is treated and advantageously smoothed, for example to remove wrinkles, lines, warts and scars therefrom, by topically applying thereto a composition which comprises at least one laser-absorbing chromophore formulated into a physiologically acceptable carrier, diluent or vehicle therefor, and laser-irradiating the skin thus treated with an intensity sufficient to locally convert the light energy into heat energy in the applied composition and advantageously effecting tissue ablation of the surface of the treated skin, said applied composition and the thickness thereof having an absorbance at the emission wavelength of the laser such that the light energy transmitted into the skin generates no undesired irreversible tissue or cell damage.

1 Claim, 3 Drawing Sheets

LASER TREATMENT/ABLATION OF SKIN TISSUE

BACKGROUND OF THE INVENTION

1. Technical Field of the Invention

The present invention relates to the application of chromophore compositions to the skin prior to laser treatment thereof. The thermal effects generated during the laser treatment are principally responsible for tissue ablation.

2. Description of the Prior Art

The nature of the interactions between the light emitted by a laser and biological tissue is complex and depends on numerous factors. At the present time, each pathology, disorder or unaesthetic characteristic of the skin requires a specific type of laser, the selection of which depends essentially on the objective which is to be achieved and the effect which is to be produced.

In particular, ablation of the outer layers of the skin (possibly extending as far as the dermis) with the aid of a laser, or smoothing of the skin, is carried out only with lasers emitting in the infrared spectrum and, thus, having a wavelength which is predominantly absorbed by water. However, the distribution of water in the skin depends on the site in question, the type of skin and the age of the individual who is to be treated. It is therefore apparent that a laser treatment of the texture of the skin which targets intracellular water is not reproducible from one individual to another. Exemplary lasers which emit in the infrared spectrum and target intracellular water include $CO_2$ (10.6 $\mu$m), Er:YAG (2.94 $\mu$m) and Ho:YAG (2.12 $\mu$m) lasers.

Lasers which emit in the visible spectrum or in the near infrared (wavelengths from 400 nm to 1000 nm), having a large penetration depth in skin, are primarily employed for treating lesions of the vascular of pigmentary type, but cannot be used for smoothing of the skin. Exemplary lasers which emit in the visible spectrum include pulsed dye lasers (585 nm) for treating vascular lesions and doubled Nd:YAG lasers (532 nm) for treating pigmentary lesions.

The clinical and histological response of skin to being irradiated with light varies considerably depending on the type of laser and the wavelength which is used. A number of effects may be generated in the target, and they directly depend on the nature of the chromophore (absorption coefficient at a given wavelength, structure and chemical composition, etc.), on the energy per unit surface area (or flux) and on the power per unit surface area (or irradiance). Studying the interaction of radiation with biological tissues makes it possible to distinguish between a number of mechanisms which occur. In the field of dermatology, the use of lasers is principally based on two types of mechanism, either the thermal effect, where the light energy is converted into heat energy, or the mechanical effect, where the light creates shockwaves.

The thermal effect results from the biological tissue absorbing the light energy associated with the laser beam and the local dissipation of this light energy in the form of heat energy. For a given wavelength, the degree to which the tissues are heated depends on the flux and the irradiance. Depending on the strength of the heating, coagulation, carbonization or ablation of the cells constituting the biological tissue may be observed. The thermal action of the laser can be divided into three principal effects, depending on the extent to which the tissue is heated and the time over which this takes place:

(1) Hyperthermia is a moderate increase in temperature, heating the tissue to temperatures of from 41° to 44° C. over several minutes. This action triggers cell damage with the membranes disappearing and the enzymes being denatured;

(2) Coagulation corresponds to necrosis without immediate tissue destruction. The temperature which the tissue reaches ranges from 50° to 100° C., over a period of time on the order of one second. This action promotes dehydration with the tissues shrinking as a result of the proteins and collagen being denatured. The necrosis is irreversible but without immediate loss of substance;

(3) Ablation corresponds to a loss of substance. The various constituents of the tissue are removed as vapor. The temperature which is attained ranges from 100° to 1,000° C., over a relatively short period of time (on the order of one-tenth of a second). Between 100° and 300° C., the tissue is removed through explosive vaporization due to the vacuoles rupturing.

The thermal transition between the irradiated zone and the healthy zone is gradual, and histological examination makes it possible to distinguish between three zones which, from the one closest to the irradiated zone to the one furthest away, correspond to: a carbonization zone or a tissue ablation zone (release of intercellular carbon at 150° C.), a coagulation zone and a hyperthermia zone.

When the heat energy is dissipated in the tissue, it may be important to match the laser irradiation period to a period referred to as the thermal relaxation time, in order to limit the thermal damage created in the adjacent tissues. From a physical point of view, this period of time is defined as the time which the tissue requires to reduce its excess temperature by 50% with respect to the initial temperature. If the duration of the laser irradiation is less than this relaxation time, the heat will not be able to diffuse inside the tissue and will remain confined in the irradiated volume. Furthermore, if, within this time, the energy deposited in the target is sufficient to increase it to a temperature very much in excess of 100° C., this will cause local vaporization of the medium. The expansion of the vapor bubble inside the tissue which has remained cool generates thermoelastic waves of weak amplitude. This process of selective photothermolysis is, for example, used for treating angiodysplasias of the skin: the erythrocytes absorb the pulse, explode, are vaporized and the rapid expansion of this vapor causes the vessel to rupture, with extravasation of the blood. Applied to the surface, this technique makes it possible to remove the target tissue locally.

Furthermore, analysis of the absorption spectrum of the various tissues indicates that the optical penetration depth of the radiation depends on the wavelength. Thus, the dissipation of energy as heat takes place in an interactive volume which depends essentially on the penetration depth of the beam (irradiated zone), the diffusion and thermal conductivity coefficients of the affected tissues, the local vascularization and ability of the target to maintain the heat stored or to lose it.

As indicated above, the thermal effect is generally obtained with an irradiance less than about $10^8$ W/cm$^2$, which corresponds to an emission time greater than or equal to about $10^{-5}$ s.

The mechanical effect is based on the possibility of concentrating a large quantity of light energy onto a sufficiently small area and for a sufficiently short period of time to cause optical breakdown of the medium. This optical breakdown results in the formation of a plasma, namely, an extensively ionized gas due to an irradiance greater than or equal to about $10^8$ W/cm$^2$ (which corresponds to an emission time less than or equal to $10^{-7}$ s, namely, a duration which is 100 times shorter than in the case of a thermal effect). The generation of shockwaves, the cavitation phenomenon and jet formation are associated with the formation of this plasma. At the boundary between the ionized medium (plasma) and the external medium, a pressure gradient is produced which results in the formation of a shockwave that will propagate into the adjacent tissues. Following this phenomenon (50–150 ns after the pulse), cavitation appears, i.e., the formation of bubbles which, for a few hundreds of microseconds, experience an oscillatory process of expansion and collapse (the bubble collapsing on itself). During these collapses, since the pressure increases considerably inside the bubble, a new shockwave is emitted.

Finally, each collapse may cause the formation of a jet if the bubble is generated close to a solid wall (for example close to a bone). This jet may then be responsible for surface damage to the solid wall (localized erosion of the solid).

Thus, U.S. Pat. No. 5,423,803 describes a process for removing a fraction of the corneal layer from the human skin using lasers which emit in the infrared spectrum (Nd:YAG, 1064 nm; $CO_2$, 10.6 $\mu$m) and have an emission time less than or equal to 50 ns. Before the laser irradiation, a composition comprising chromophores is applied to the skin which is to be treated. By employing either ultrasound or a laser, these chromophores are inserted into the intracellular spaces of the corneal layer. This treated area of the skin is then irradiated by a laser beam having sufficient energy to ionize the chromophores (after optical breakdown). As described above, the ionization of the chromophore leads to the formation of shockwaves (mechanical effect) which are responsible for ablating the first three cellular levels of the corneal layer. Since this effect is based on the emission of shockwaves, it presents the drawback of generating undesired irreversible lesions in the tissues adjacent to the area which is treated. Furthermore, the effectiveness of this treatment is spatially and qualitatively limited by the penetration of the chromophores into the corneal layer.

SUMMARY OF THE INVENTION

Accordingly, a major object of the present invention is the provision of an improved process for smoothing mammalian, characteristically human skin using a laser which emits in the visible spectrum.

Another object of the present invention is the provision of an improved process for smoothing human skin using a laser which emits in the infrared spectrum and which is reproducible.

Another object of this invention is the provision of an improved process for smoothing human skin which avoids the formation of undesired irreversible lesions.

Briefly, the present invention features a process for smoothing human skin by converting light energy of laser radiation into heat energy at the surface of the skin employing a composition containing at least one chromophore, comprising (1) topically applying a composition which, in a physiologically acceptable carrier, comprises at least one chromophore on to the surface of the skin, said composition and its applied thickness having an absorbance at the emission wavelength of the laser such that the light energy transmitted into the skin generates no undesired irreversible tissue or cell damage, and (2) then laser-irradiating said surface of the skin, the irradiation provided by the laser effecting local conversion of the light energy into heat energy in the area of the applied composition.

More particularly, the heat energy produced in the composition during a single laser exposure will be propagated by conduction inside the skin, locally increasing the temperature to more than 100° C. in order to obtain tissue ablation.

The present invention thus also features the use of at least one chromophore for the formulation of compositions destined to be applied topically to the surface of the skin prior to laser-irradiation thereof, the irradiation via the laser locally converting the light energy into heat energy in the area of applied composition, this heat energy effecting tissue ablation of the skin lying under the treated surface.

Preferably, this composition and its applied thickness have an absorbance at the emission wavelength of the laser such that the light energy transmitted into the skin generates no undesired irreversible tissue or cell damage.

Figure 1:
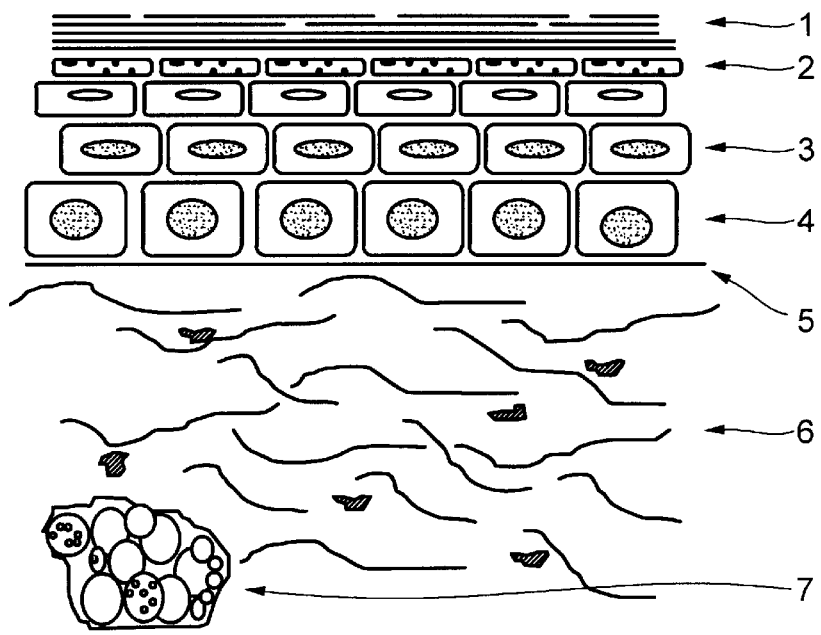
FIGS. 1–6 are schematic representations of the skin of a nude or hairless rat, progressively illustrating the method of laser treatment/ablation of skin tissue according to the present invention.

DETAILED DESCRIPTION OF BEST MODE AND SPECIFIC/PREFERRED EMBODIMENTS OF THE INVENTION

More particularly according to the present invention, after tissue ablation, fresh skin can form with a younger and/or less inelegant appearance, which is deemed "smoothing" of the skin. More especially, this technique may make it possible to remove an unaesthetic characteristic of the skin, for example wrinkles, lines, warts, atrophic and/or hypertrophic scars. Further, this treatment may be used as such or as a supplement to a medicinal or therapeutic treatment for treating skin pathologies, such as, in particular, rhinophyma, hyperkeratosis, hyperproliferations of the skin, a patch of psoriasis, skin cancer, actinic keratosis, or keloids.

Too, the tissue ablation may make it possible to increase the penetration of cosmetic or pharmaceutical, and more particularly dermatological, active agents. In this instance, after irradiation and before the fresh skin has been formed completely, a cosmetic or pharmaceutical composition comprising at least one active agent is applied. Exemplary active agents include those used cutaneously as a medication with a view to local and/or systemic delivery, especially, for example, retinoic acid and its derivatives (retinoids), benzoyl peroxide, antibiotics, corticosteroids, fungicides, vitamins D3 or D2 and derivatives thereof.

The present invention also features a cosmetic treatment, in particular for reducing wrinkles and fine lines, comprising (1) topically applying a composition which, in a physiologically acceptable carrier, contains at least one chromophore, onto the surface of the skin, said composition and its applied thickness having an absorbance at the emission wavelength of the laser such that the light energy transmitted into the skin generates no undesired irreversible tissue or cell damage, and (2) laser-irradiating said treated surface of the skin, the irradiation provided by the laser locally converting of the light energy into heat energy in the applied composition, and this heat energy effecting tissue ablation of the skin lying under said treated surface.

The thermal effect, which corresponds to the conversion of the light energy into heat energy, is as described above. This thermal effect is therefore generally provided by a laser whose irradiance is less than about $10^8$ W/cm$^2$, which corresponds to an emission time greater than or equal to about $10^{-5}$ s. Preferably, it is provided by a laser whose irradiance is less than or equal to about $10^7$ W/cm$^2$.

Preferably, the irradiance is greater than or equal to 0.5 W/cm$^2$, advantageously greater than or equal to 10 W/cm$^2$, and yet more advantageously greater than or equal to 100 W/cm$^2$.

Preferably, the emission time is less than or equal to 100 s and advantageously less than or equal to 10 s.

The light energy emitted by the laser is thus converted into heat energy in the composition applied to the skin, through absorption by the chromophores present in this composition.

More particularly, the heat energy makes it possible to obtain only tissue ablation of the corneal layer and the epidermis. Under these conditions, the dermis may or may not be coagulated, as described above, depending on the heat energy transmitted to the skin. In certain treatments, for example increasing the penetration of active agents, it is not necessary for the superficial dermis to be coagulated.

The chromophores which can be used according to the present invention are advantageously those which permit a composition comprised thereof to have an absorbance at the emission wavelength of the laser such that the light energy transmitted into the skin generates no undesired irreversible tissue or cell damage. More particularly, exemplary are the inorganic chromophores, such as carbon black, graphite, black iron oxide and red iron oxide, and organic chromophores, such as melanin, indocyanine green, dyes or any other inert chemical entity which absorbs sufficiently at the wavelength in question, (for example, at 1064 nm: silicon derivatives, cholesterol derivatives, phosphates, sulfates). Inorganic chromophores are the preferred.

These chromophores may be dispersed in an oily and/or aqueous support (emulsions, gels, ointments, polymer dispersions, any vesicular systems, aerosols, suspensions in a liquid medium which may or may not form films, optionally presented in aerosol form) or dissolved in any types of physiologically acceptable carriers, diluents or vehicles.

Preferably, the chromophores and/or the compositions comprising same are selected and/or are formulated in such manner that the chromophores do not penetrate through the skin. The chromophores may thus have a suitable particle size such that they do not penetrate through the skin, or the composition comprises chromophores in the form of aggregates, preventing them from penetrating through the skin.

The undesired irreversible tissue or cell damage corresponds, in particular, to deterioration of the capillary vessels lying in the dermis, due to coagulation of hemoglobin or irreversible destruction of melanocytes, Langerhans' cells, keratinocytes or fibroblasts, more particularly their precursors, especially by ablation of the endogenous chromophores contained in these cells or their precursors, such as water, melanine or proteins.

All types of lasers emitting either in the visible or in the infrared spectrum may be used in step (2) so long as they make it possible to generate a thermal effect. Examples of lasers which emit in the visible spectrum include a pulsed dye laser (585 nm), a ruby laser (694 nm) and a doubled Nd:YAG laser (532 nm), and for lasers which emit in the infrared spectrum, $CO_2$ (10.6 μm), Er:YAG (2.94 μm), Ho:YAG (2.12 μm) and Nd:YAG (1.06 μm) lasers.

The absorbance of the composition and the thickness with which it is applied to the surface of the skin depends on the emission wavelength of the laser, as well as on the physicochemical characteristics of the formulation. More specifically, the absorbance varies depending on the type of chromophore, its particle size, the quality of the dispersion of this product, the concentration and the formulation of the composition; thus, by way of example, carbon black formulated at 2.5% does not, under certain conditions, have the same absorption spectrum as a formula with 0.25%.

Thus, for a given concentration of pigment in a given carrier, and under the same experimental conditions, an increasing dispersion quality of the pigment (use of tricylinder, ultraturax, passing through a pigmentary paste) improves the absorption of light.

In the case of a laser which emits in the visible spectrum or in the near infrared (wavelength less than 1 μm), the composition which comprises at least one chromophore and is placed between the radiation from the laser and the skin allows melanin, hemoglobin and oxyhemoglobin, which are the principal endogenous chromophores which absorb at these wavelengths, to be protected from the laser irradiation. Tissue ablation is thus carried out while protecting the endogenous compounds of the dermis and depends principally only on the composition used according to the invention, the thickness of the film of this composition on the skin and, of course, the parameters of the laser which is used.

In the case of a laser which emits in the infrared spectrum (wavelength greater than 1 μm), the composition which comprises at least one exogenous chromophore and is placed between the radiation of the laser and the skin makes it possible for the result obtained on the skin to depend no longer on the distribution of the water contained in the tissues. Indeed, the distribution of the water in these tissues depends both on the site in question, the type of skin and the age of the patient who is to be treated. The result which is obtained thus depends principally only on the composition according to the invention, the thickness of this composition on the skin and, of course, the parameters of the laser which is used.

Thus, for a given treatment (loss of material and depth to be reached), the result is achieved by defining, for the user of a specific laser, the irradiance and the flux as a function of the composition and the thickness with which it is to be applied to the surface of the skin.

FIGS. 1 to 6 illustrate the invention more clearly, but without limiting its scope. These figures correspond to a schematic representation of the skin of a nude or hairless rat.

In FIG. 1: 1 represents the corneal layer, 2 the granular layer, 3 the prickle cell layer, 4 the basal cell layer, 5 the basement membrane, 6 the dermis and 7 a sebaceous gland in the dermis.

Figure 2:
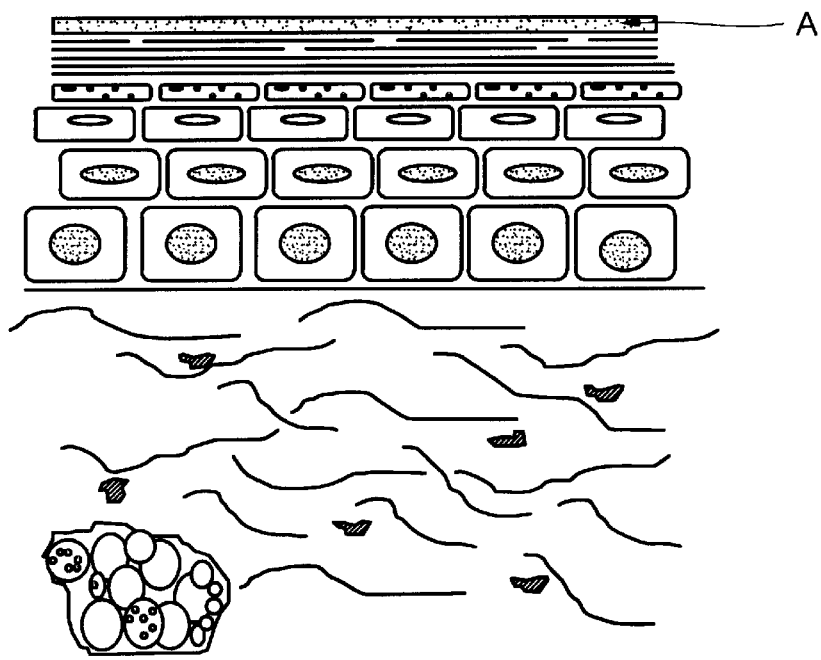

FIG. 2 corresponds to step (1) of the process: application of composition A comprising the chromophores to the surface of the skin.

Figure 3:
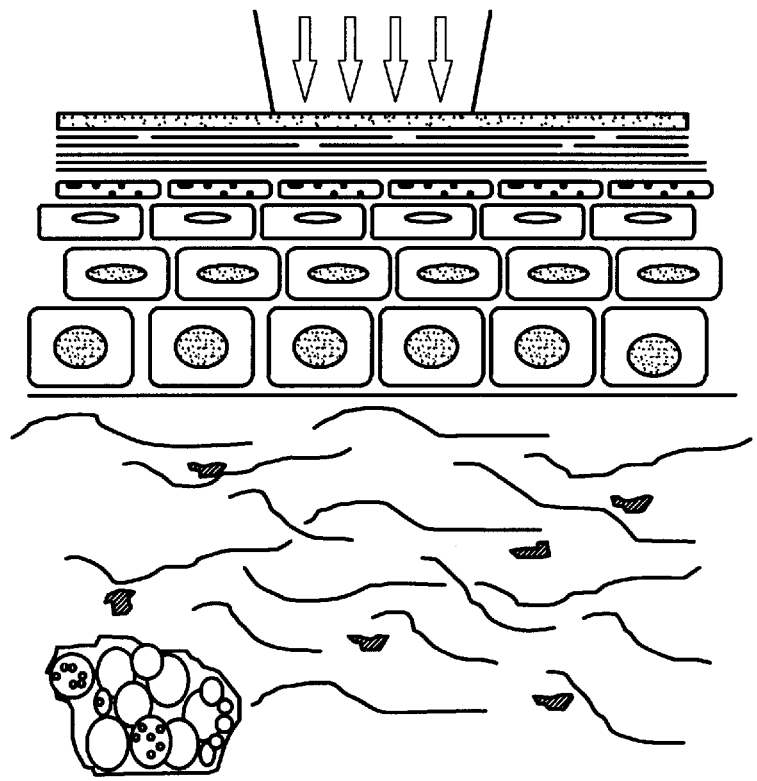

FIG. 3 corresponds to step (2) of the process: application of light radiation using a laser.

Figure 4:
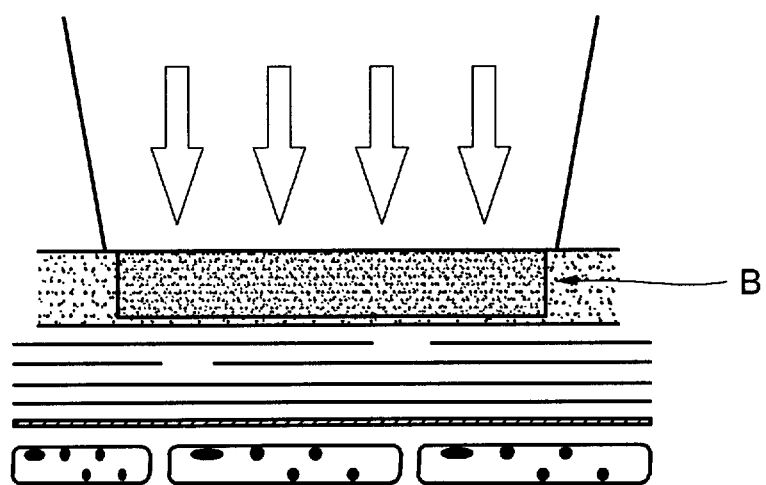

FIG. 4 represents the volume B of interaction of the composition applied to said surface of the skin with the light energy, converting it into heat energy.

Figure 5:
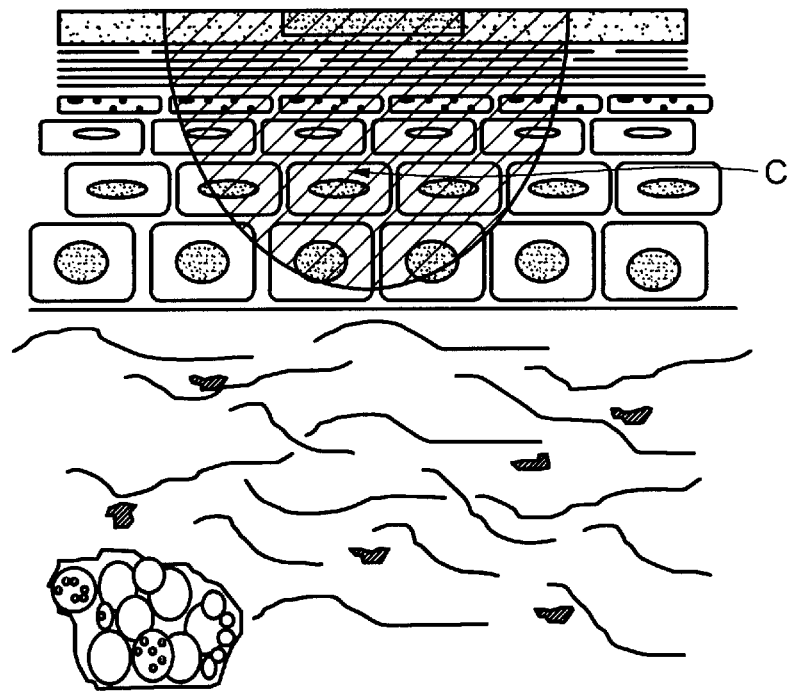

FIG. 5 represents the volume C (hatched area) heated by thermal conduction.

Figure 6:
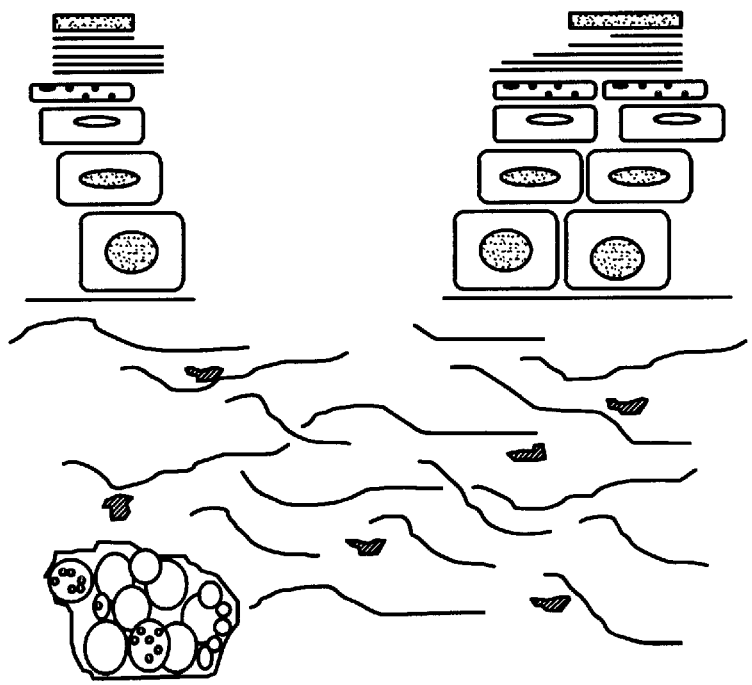

FIG. 6 represents tissue ablation of the skin, which continues down to the basement membrane.

More particularly, the irradiance and the flux are selected such that the duration of the laser irradiation is less than the thermal relaxation time of the skin which is treated. The heat can then diffuse inside the skin, but remains confined in a small volume, making the tissue ablation more selective.

Advantageously, a composition, more particularly a film-forming composition (a composition which dries after application), which does not absorb light at the wavelength employed, may be applied over the composition according to the invention, before the laser radiation is initiated. The object of this addition is to confine the energy which is released to a smaller interactive volume and to amplify the thermoelastic waves emitted during the tissue ablation. It is thus possible, with a minimum of light energy, for the tissue to be ablated while limiting the damage generated in the adjacent tissues.

In one embodiment of the invention, the laser may be connected to a device which permits the laser to be moved over an area larger than that which corresponds to the laser beam area applied to the skin, in order to allow said surface to be treated uniformly and reproducibly. The device which is used may, in particular, be as described in U.S. Pat. No. 5,330,517.

In order to further illustrate the present invention and the advantages thereof, the following specific examples are given, it being understood that same are intended only as illustrative and in nowise limitative.

In said examples to follow, as above, all parts and percentages are given by weight, except where otherwise indicated.

EXAMPLE 1:

O/W emulsion based on red iron oxide (5%):

| | Components | % |
|---|---|---|
| (a) | Lanol CTO (Seppic) cetylstearyl alcohol | 7 |
| (b) | Geleol (Gattefossé) glyceryl stearate | 2 |
| (c) | Cetyl alcohol | 1.5 |
| (d) | DC 200, 300 cp polydimethylsiloxane | 1.5 |
| (e) | Polysynlane (NOF) hydrogenated isoparaffin | 15.1 |
| (f) | Sicovit red 30E172(BASF) red iron oxide | 5 |
| (g) | Glycerol | 20.1 |
| (h) | Water | 47.8 |

EXAMPLE 2:

Aqueous gel based on carbon black (2.5%):

| | Components | % |
|---|---|---|
| (a) | Derussol A (Deggussa) aqueous dispersion of carbon black | 16.65 |
| (b) | Water | 72.85 |
| (c) | Aérosil 200 (Degussa) | 7.5 |
| (d) | Propylene glycol | 2 |
| (e) | Poloxamer 182 | 1 |

EXAMPLE 3:

Ointment based on carbon black (2.5%):

| | Components | % |
|---|---|---|
| (a) | FW1 (Degussa) carbon black | 2.5 |
| (b) | Polysynlane (NOF) | 19.4 |
| (c) | Suitable lipophilic dispersing agent | 0.63 |
| (d) | Petroleum jelly codex | 77.47 |

EXAMPLE 4:

Film-forming solution based on carbon black (2.28%):

| | Components | % |
|---|---|---|
| (a) | Derussol A (Degussa) | 15.2 |
| (b) | Eudragit NE 30 D (Rohm and Haas) | 34.7 |
| (c) | Water | 50.1 |

EXAMPLE 5:

Treatment for smoothing of the skin:

The smoothing of the skin utilizing a pharmaceutical preparation according to the invention is represented in FIGS. 1 to 6.

FIG. 1 depicts the structure of the epidermis and the dermis of a nude or hairless rat.

Application of the pharmaceutical preparation:

Topical formulation was applied to the surface of the skin (on the corneal layer) of a nude or hairless rat. The chromophore contained in the composition remained at the surface of the corneal layer and was not distributed therein (FIG. 2).

Laser irradiation:

Next, the surface of the skin was irradiated using a doubled Nd:YAG laser (532 nm) having an emission time of more than 1 $\mu$s (FIG. 3). Since the mechanism employed was the thermal effect, the irradiation was less than $10^7$ W/cm$^2$. The compositions which were applied (compositions set forth in Examples 1 or 2) and the thickness to which each was applied had an absorbance such that the light energy transmitted to the tissue (epidermis, dermis) was not sufficient to generate irreversible tissue or cell damage. With the composition being placed between the laser radiation and the skin, the melanin present in the epidermis as well as the oxyhemoglobin and the hemoglobin which are contained in the vessels were protected from the irradiation.

If a sufficient thickness of composition was applied (about 100 $\mu$m for the compositions set forth in Examples 1 and 2), the light energy absorbed by the chromophore contained in the compositions was converted locally (in the composition) into heat energy (FIG. 4). The heat produced in the composition during a single laser exposure propagated by conduction inside the skin (FIG. 5), locally increasing the temperature to more than 100° C. in order to obtain tissue ablation (FIG. 6).

More particularly, when the composition described in Example 2 was topically applied to the surface of the skin of a nude rat, at a thickness of about 100 $\mu$m, with an irradiance of 450 W/cm$^2$ and a flux of 25 J/cm$^2$, it was possible to coagulate the superficial dermis over 25 to 50 $\mu$m and at the same time ablate the epidermis down to the basal layer. After 8 to 10 days, the skin of the rat reforms through the cicatrization phenomenon. The corneal layer, like the rest of the skin, was restored by this phenomenon.

The use of other exogenous chromophores modified the irradiation conditions of the composition applied to the corneal layer for the same result as above. By way of example, using the composition described in Example 1 required the same irradiance (450 W/cm$^2$), but a flux which was almost two times as great in order to obtain the same result.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for treating mammalian skin in need of such treatment, comprising topically applying to said skin a composition which comprises at least one laser-absorbing chromophore formulated into a physiologically acceptable carrier, diluent or vehicle therefor, wherein the resultant chromophore containing formulation is formulated such that said chromophores do not penetrate the skin, and laser-irradiating said skin thus treated with an intensity sufficient to locally convert the light energy into heat energy in the applied composition, said applied composition and the thickness thereof having an absorbance at the emission wavelength of the laser such that the light energy transmitted into the skin generates no undesired irreversible tissue or cell damage, said laser-irradiating effecting tissue ablation of the surface of said treated skin, and wherein said method further comprises overcoating said chromophore composition with a film-forming composition which does not absorb lignt at the wavelength of the laser.

* * * * *